United States Patent [19]

Montalbano et al.

[11] Patent Number: 4,583,550
[45] Date of Patent: Apr. 22, 1986

[54] ACCESS WINDOW ASSEMBLY FOR A BODY CAST

[75] Inventors: Anthony P. Montalbano, Glen Cove; David E. Conroy, City Island, both of N.Y.

[73] Assignee: Biolectron, Inc., Hackensack, N.J.

[21] Appl. No.: 607,463

[22] Filed: May 7, 1984

[51] Int. Cl.[4] ............................................. A61B 5/04
[52] U.S. Cl. .................................... 128/644; 128/787; 128/802
[58] Field of Search .................... 128/419 F, 787, 802, 128/803, 792, 639, 644

[56] References Cited

U.S. PATENT DOCUMENTS

| 2,367,690 | 1/1945 | Purdy | 128/132 |
|---|---|---|---|
| 2,523,837 | 9/1950 | Luger . | |
| 2,855,922 | 10/1958 | Schroeder . | |
| 3,279,468 | 10/1966 | Le Vine | 128/792 |
| 3,508,541 | 4/1970 | Westbrook et al. | 128/644 |
| 3,967,628 | 7/1976 | Verdenbregt | 128/802 |
| 4,019,506 | 4/1977 | Eschmann . | |
| 4,323,076 | 4/1982 | Sams | 128/644 |
| 4,365,637 | 12/1982 | Johnson | 128/644 X |
| 4,445,518 | 5/1984 | Eggli et al. | 128/802 X |
| 4,448,199 | 5/1984 | Schmid | 128/644 X |
| 4,456,001 | 6/1984 | Pescatore | 128/802 X |
| 4,491,128 | 1/1985 | Haschke | 128/419 F X |
| 4,535,779 | 8/1985 | Ober | 128/802 X |

*Primary Examiner*—Edward M. Coven
*Attorney, Agent, or Firm*—Brumbaugh, Graves, Donohue & Raymond

[57] ABSTRACT

A device for mounting a treatment electrode on the skin of a patient in an area covered by a body cast comprises an access window secured intermediate the ends of a relatively flexible band embedded in the body cast. The access window has a releasably latched cap with a central opening in which is secured a flexible diaphragm for supporting an electrode in contact with the adjacent skin area of the patient. The cap opening is normally tightly closed by a removable cover.

2 Claims, 5 Drawing Figures

ACCESS WINDOW ASSEMBLY FOR A BODY CAST

BACKGROUND OF THE INVENTION

This invention relates to a device adapted to be incorporated in a body cast to mount an object such as a treatment electrode in predetermined relation to the body skin of a patient. More particularly, it relates to a device of this general character providing a securely reclosable opening in the cast facilitating ready access to the object and to the skin of the patient when needed for adjustment or cleaning, for example.

Remarkable results are being gotten today with the use of electrical stimulation in the treatment of bone fractures and other bone diseases. In one highly successful technique, the stimulation is effected by an ultrasonic electric signal applied to the skin of the patient in the vicinity of the bone fracture. Since a fracture must usually be immobilized in a cast, it has not always been easy to arrange for effective treatment with electrical stimulation. It is not desirable to embed the electrode under the cast since effective cleaning and adjustment are then not possible. Moreover, attempts that have been made to treat a patient with an electrode mounted in an opening cut in a cast have not been entirely satisfactory because of the difficulty of maintaining uniform adjustment of the electrode and preventing tampering by the patient.

It is an object of the invention, accordingly, to provide a new and improved device for mounting a treatment electrode or the like in a body cast that is free from the above-noted deficiencies of the prior art.

Another object of the invention is to provide a new and improved mounting device of the above character which affords ready access to the treatment electrode and the skin of the patient for adjustment or cleaning, yet is tamper-proof and reliable in operation.

BRIEF SUMMARY OF THE INVENTION

These and other objects of the invention are attained by providing a mounting device having a generally circular access window secured intermediate the ends of a flat, relatively flexible band that is adapted to be embedded in the cast as it is formed on the body of the patient. The access window has a hinged cap provided with a releasable latch for retaining it securely in the closed position. The cap has a central opening in which is secured a flexible diaphragm together with means releasably retaining a treatment electrode or the like on the underside thereof and the opening in the cap is normally tightly closed by a removable cover.

In use, after the mounting device is embedded in the cast, the cap is opened, the cover is removed from the cap and flexible spacer material is disposed above the electrode retainer so that when the cover is replaced and the cap is closed, the electrode carried by the diaphragm will be correctly positioned in relation to the skin of the patient for the treatment to be carried out. Thereafter, the access window can be readily opened to permit inspection or cleaning of the electrode or the skin of the patient merely by releasing the cap latch to permit the cap to be moved to the open position.

The invention may be better understood from the following detailed description, taken in conjunction with the accompanying drawings in which.

DESCRIPTION OF THE PREFERRED EMBODIMENTS

Figure 1:
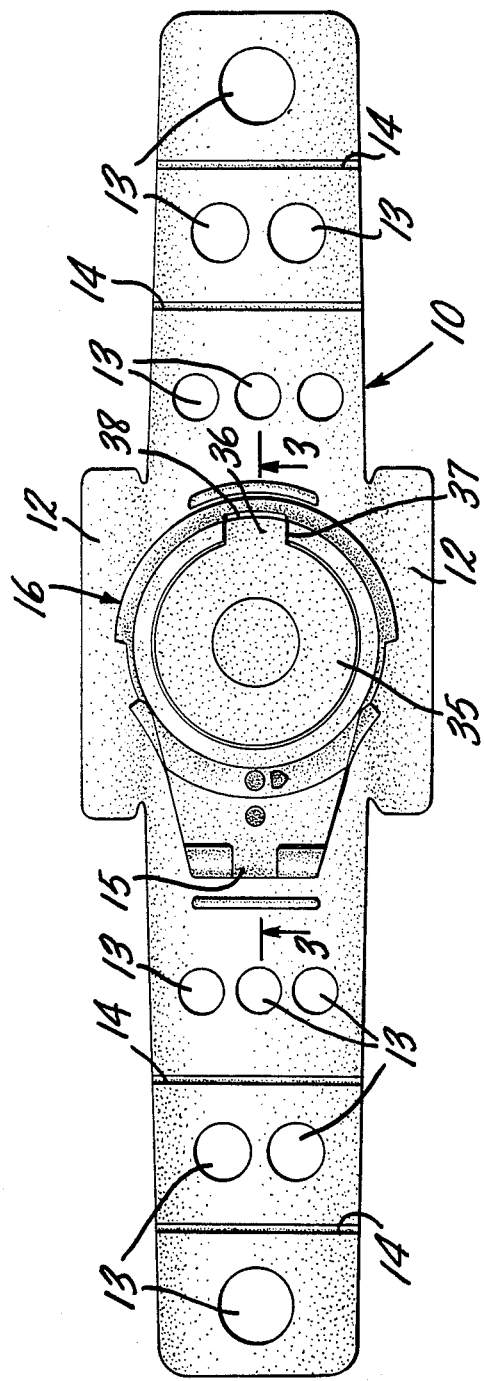
FIG. 1 is a plan view of one form of mounting device constructed according to the invention.
Figure 2:
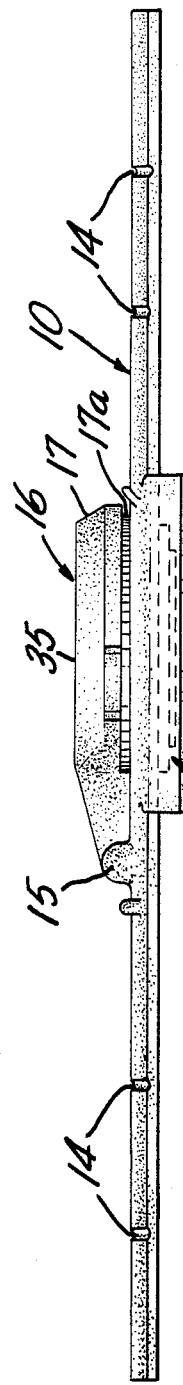
FIG. 2 is a side view of the mounting device shown in FIG. 1.

Referring now to FIG. 1, a typical mounting device according to the invention comprises an elongated band 10 formed with a circular, relatively rigid access window 11 intermediate its ends. The band 10 has short, downwardly angled, lateral extensions 12 on opposite sides of the access window 11 and it is preferably formed with a number of openings 13 to aid in retaining it securely in a conventional plaster cast. The band 10 may also be provided with spaced transverse grooves 14 to enable segments to be broken off to adjust the length of the band to the size of the cast.

Hinged at 15 on the band 10 on one side of the access window 11 is a cap 16 formed with upper and lower ring members 17 and 17a which are tightly secured together. The cap 16 is mounted for limited rotation about the axis of the window 11 from a position in which it is latched to the band 10 to an unlatched position. To this end, the upper and lower ring members 17 and 17a are provided with arcuate flange portions 18 and 19, respectively, adapted to cooperate with a matching arcuate groove 20 and a flange 21, respectively, on the hinge 15 to permit limited rotation of the cap in opposite directions.

At the opposite end of the lower cap ring 17a is formed a latch member 22, which when the cap 16 is rotated counterclockwise to its limit (the unlatched position) is located so as to be able to enter a matching recess 23 formed in the side wall of the access window 11. With the latch member 22 inserted in the recess 23, rotation of the cap 16 clockwise to its opposite limit (the latched position) locates the latch member 22 under the adjacent edge of the band 10 so that the cap 16 is locked in the closed position. Preferably, conventional snap retainer means (not shown) may be provided for retaining the latch member 22 releasably in the locked position.

Clamped between the upper and lower cap rings 17 and 17a is a diaphragm 24 made of suitable flexible material having a flat, central, upper portion 25 surrounded by a downwardly depending annular portion 26. Secured to the diaphragm upper portion 25 is a retainer for an electrode or the like comprising an upper disk 27 to which is fastened a downwardly extending cylindrical retainer member 28. The retainer member 28 has an opening 29 at its lower end adapted to receive a snap-in connector 30 on an electrode holder 31.

The electrode holder 31 may be a plastic disk 32 having molded in the lower face thereof a thin contact electrode 33 made of stainless steel, for example. The electrode 33 is connected to an insulated conductor 34 embedded in the holder which extends through the band 10 so as to be accessible from the outside of the cast in which the latter is mounted.

The central opening in the upper cap ring 16 is closed by a snugly fitting snap-in cover 35 made of suitable material such as plastic foam, for example. As best shown in FIG. 1, the cover 35 may be provided with a tab 36 extending into a matching recess 37 in the upper cap ring 16. A narrow slot 38 may be provided between the end of the tab 36 and the recess 37 for the insertion of a thumbnail to facilitate removal of the cover 35 as required.

Figure 3:
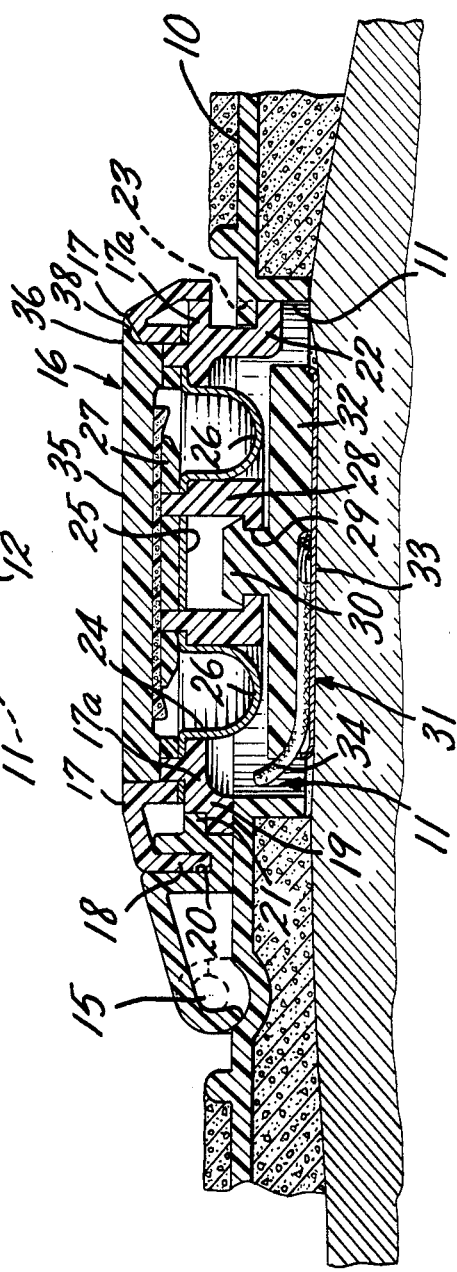
FIG. 3 is an enlarged partial view in section taken along the line 3—3 of FIG. 1 and looking in the direction of the arrows, showing details of the access window and the way the device may be embedded in a cast on a body member.

In use, the band 10 is embedded in the conventional body cast used to immobilize a bone fracture so that the bottom access window 11 is spaced a short distance above the skin of the patient, as shown generally in FIG. 3. The cover 35 is removed and the cap 16 rotated counterclockwise to the unlatched position so that it can be opened. An electrode holder 31 with an electrode 33 mounted thereon is snapped into the retainer member 28. A spacer or spacers 38 are then placed on top of the retainer disk 27 so that when the cover 35 is replaced and the cap 16 is returned to its closed latched position, the electrode 33 will be in proper contact with the skin of the patient as required for the electric stimulation procedure. In practice, the body cast assemblies are usually mounted on opposite sides of the body cast for treatment of a fracture or the like therebetween.

Figure 4:
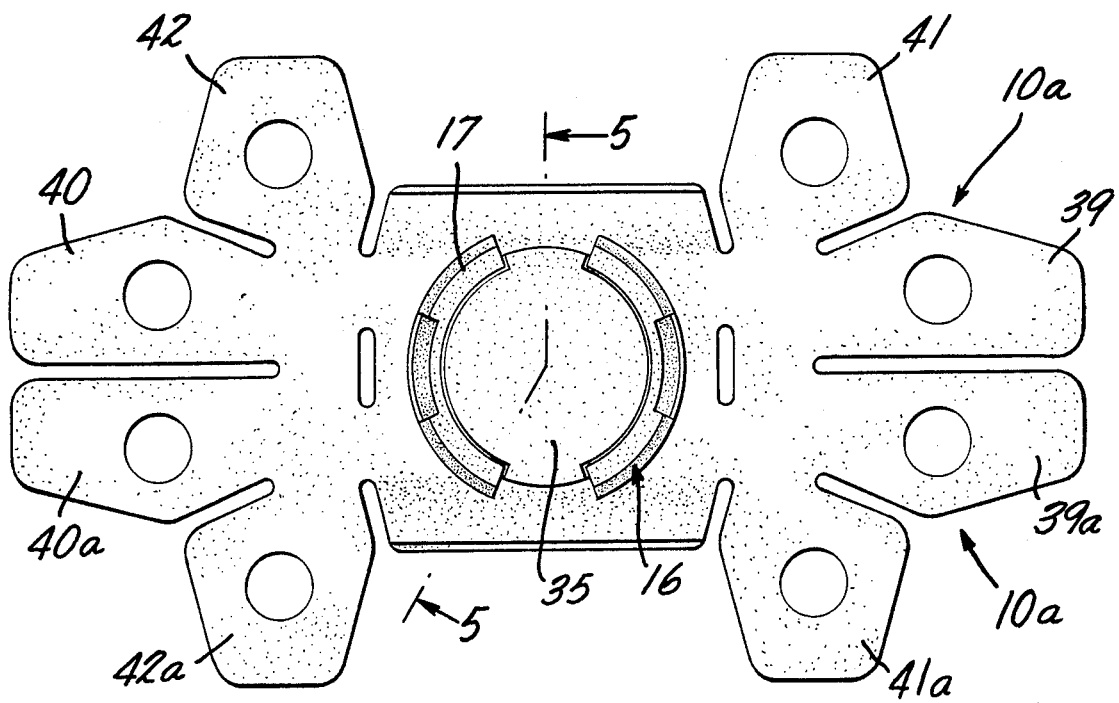
FIG. 4 is a plan view of a modified form of mounting device suitable for use with navicular fractures where the size of the cast is usually small.
Figure 5:
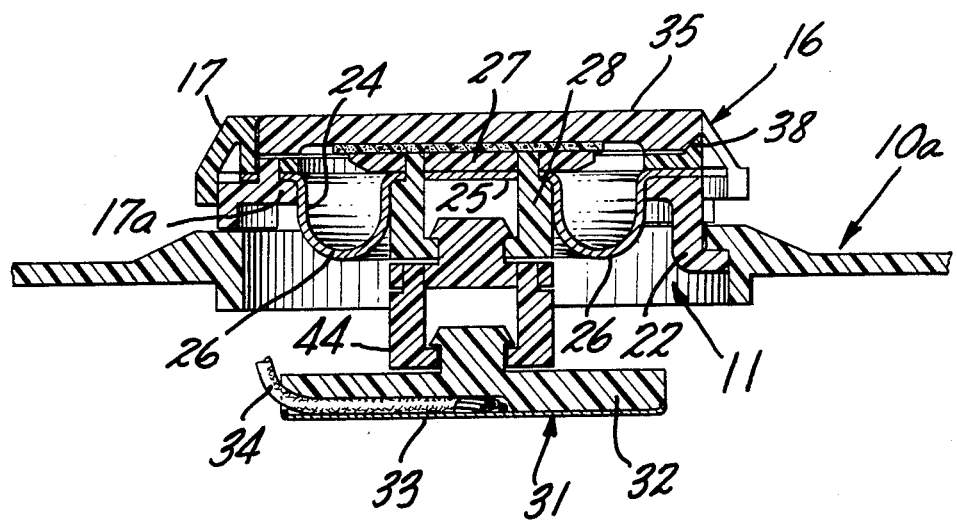
FIG. 5 is an enlarged partial view in section taken along the line 5—5 of FIG. 4, looking in the direction of the arrows.

The modification shown in FIGS. 4 and 5 is intended to be used in the treatment of navicular fractures, for example, where the space available is usually limited. In this form, the access window 11 is mounted on a band 10a formed with a plurality of thin, very flexible, longitudinal tabs 39, 39a, 40, 40a and lateral tabs 41, 41a, 42 and 42a to facilitate incorporating it in a plaster cast on the wrist of a patient, for example. The access window 11 is substantially the same as in FIG. 1 except that the cap 16 is not hingedly mounted on the band. It may be secured to the latter by cooperating latches like the latch member 22 in FIG. 1 located on opposite sides of the access window 11 so that when it is rotated counterclockwise it is unlatched and can be lifted off the window 11. Also, an electrode retainer extension 44 (FIG. 5) may be interposed between the retainer member 28 and the electrode 31, if necessary to lower the latter sufficiently when mounted in a thick cast to put the electrode in contact with the skin of the patient.

The invention thus provides simple and highly effective means for mounting a treatment electrode or the like in a body cast. The provision of an access window with an openable closure as described enables easy adjustment of the position of the electrode in relation to the skin of the patient, while affording easy access by a doctor or technician to the electrode and to the electrode and the patient's skin for inspection and cleaning as desired. Moreover, with the cap closed and latched, the electrode is maintained in proper contact with the skin of the patient and essentially tamperproof.

The specific embodiments described are intended to be merely illustrative and modifications in form and detail are possible within the scope of the appended claims.

We claim:

1. An access window assembly for mounting in a body cast comprising
    a band having end members and side members for incorporation in a body cast,
    means forming a shallow, generally circular opening intermediate the ends of said band providing an access window therein,
    a cap member for said access window comprising ring means coaxial therewith and mounted for limited rotation in opposite directions thereover,
    cooperating means on said band and on said ring means effective to lock said ring means to the under side of said band upon rotation of said ring means in one direction and to unlock said ring means and said band upon rotation of said ring means in the opposite direction,
    means mounting a flexible diaphragm in said ring means near the upper end thereof,
    means securing an electrode releasably to said diaphragm in said access window,
    a snap-in cover snugly fitted in the upper end of said ring means and closing the upper end of the opening therein, and
    spacer means interposed between said cover and said diaphragm for adjusting the position of said electrode to a desired level in said access window.

2. An access window assembly as defined in claim 1 in which said cap member is mounted on the band by hinge means so as to be movable to open and close said access window, and said ring means is mounted to said hinge means for limited rotation in opposite directions with respect thereto.

* * * * *